US008573076B2

(12) United States Patent
Sarr et al.

(10) Patent No.: US 8,573,076 B2
(45) Date of Patent: Nov. 5, 2013

(54) NON-DESTRUCTIVE INSPECTION SYSTEMS AND METHODS THAT INCORPORATE INTERCHANGEABLE PROBES

(75) Inventors: Dennis P. Sarr, Kent, WA (US); James C. Kennedy, Renton, WA (US)

(73) Assignee: The Boeing Company, Chicago, IL (US)

( * ) Notice: Subject to any disclaimer, the term of this patent is extended or adjusted under 35 U.S.C. 154(b) by 255 days.

(21) Appl. No.: 13/179,878

(22) Filed: Jul. 11, 2011

(65) Prior Publication Data

US 2013/0014600 A1 Jan. 17, 2013

(51) Int. Cl.
*G01N 29/00* (2006.01)
*G01D 21/00* (2006.01)

(52) U.S. Cl.
USPC ........................................ 73/865.8; 73/866.5

(58) Field of Classification Search
USPC ............................................. 73/866.5, 865.8
See application file for complete search history.

(56) References Cited

U.S. PATENT DOCUMENTS

| | | | |
|---|---|---|---|
| 4,470,122 A | 9/1984 | Sarr | |
| 4,807,476 A | 2/1989 | Cook et al. | |
| 4,848,159 A | 7/1989 | Kennedy et al. | |
| 6,641,535 B2 | 11/2003 | Buschke et al. | |
| 6,722,202 B1 | 4/2004 | Kennedy et al. | |
| 7,231,826 B2 | 6/2007 | Bossi et al. | |
| 7,249,512 B2 | 7/2007 | Kennedy et al. | |
| 7,263,889 B2 | 9/2007 | Kennedy et al. | |
| 7,430,913 B2 | 10/2008 | Sarr | |
| 7,444,876 B2 | 11/2008 | Sarr et al. | |
| 7,508,971 B2 | 3/2009 | Vaccaro et al. | |
| 7,640,810 B2 | 1/2010 | Kennedy et al. | |
| 7,640,811 B2 | 1/2010 | Kennedy et al. | |
| 7,698,947 B2 | 4/2010 | Sarr et al. | |
| 7,743,660 B2 | 6/2010 | Marsh et al. | |
| 2007/0039390 A1* | 2/2007 | Duncan et al. | 73/606 |
| 2008/0210009 A1* | 9/2008 | Tanishiki | 73/588 |
| 2008/0223152 A1* | 9/2008 | Georgeson et al. | 73/862.041 |
| 2009/0245930 A1* | 10/2009 | Baulier et al. | 403/321 |
| 2010/0009825 A1* | 1/2010 | Norton et al. | 483/58 |
| 2010/0095775 A1 | 4/2010 | Sarr et al. | |
| 2010/0197472 A1* | 8/2010 | Strotzer et al. | 483/10 |
| 2011/0146424 A1 | 6/2011 | Sarr et al. | |
| 2011/0171738 A1* | 7/2011 | Aoki et al. | 436/86 |

* cited by examiner

*Primary Examiner* — Hezron E Williams
*Assistant Examiner* — David Z Huang
(74) *Attorney, Agent, or Firm* — Armstrong Teasdale LLP

(57) ABSTRACT

A non-destructive inspection (NDI) device is described that includes a robotic arm, a storage device proximate the robotic arm, and a plurality of NDI probe assemblies disposed within the storage device. Each NDI probe assembly includes at least one transducer operable for NDI of a part and a tool operable as a mechanical interface between the robotic arm and the corresponding NDI probe assembly. Each NDI probe assembly is configured for a specific NDI task, for NDI of a part, and the robotic arm is operable for selectively engaging the tools and movement of the probe assemblies for the NDI of at least a portion of a part.

12 Claims, 19 Drawing Sheets

NON-DESTRUCTIVE INSPECTION SYSTEMS AND METHODS THAT INCORPORATE INTERCHANGEABLE PROBES

BACKGROUND

The field of the disclosure relates generally to non-destructive inspection (NDI) equipment and processes, and more particularly to NDI systems and methods that incorporate interchangeable probes.

Part of the fabrication process for composite parts, for example, primary structural composite parts and composite rib parts for an aircraft, includes a non-destructive inspection (NDI) process. However, in one example fabrication, the composite ribs are not identical to one another. That is, rib number two is a completely different size, for example, than rib number five. Further in this example fabrication, ribs destined for the right side of the aircraft are different from the ribs destined for the left side of the aircraft.

Currently, NDI is performed using an x-y-z scanner with NDI probes attached to an end of the effector. The NDI probes are interchanged by an operator to perform the various NDI tests associated with a part. Separate inspection systems for individual components, and operator interchanging of probes, is cost prohibitive. Further, as much NDI is performed in deep water tanks, the expense associated with such tanks is a cost that companies would like to avoid.

Robotic inspection with ultrasonic NDI systems has always had limitations due to the sensitivity of the probe heads to electrical connection/disconnection. As described above, however, having a different probe head for every inspection condition would result in a heavy and complex end effector that would impact the size and cost of the robot.

BRIEF DESCRIPTION

In one aspect, a non-destructive inspection (NDI) device is provided that includes a robotic arm, a storage device proximate the robotic arm, and a plurality of NDI probe assemblies disposed within the storage device. Each NDI probe assembly includes at least one transducer operable for NDI of a part and a tool operable as a mechanical interface between the robotic arm and the corresponding NDI probe assembly. Each NDI probe assembly is configured for a specific NDI task, for NDI of a part, and the robotic arm is operable for selectively engaging the tools and movement of the probe assemblies for the NDI of at least a portion of a part.

A method for non-destructive inspection (NDI) of a part that incorporates multiple structural features is provided. The method includes selecting an NDI probe assembly from a plurality of NDI probe assemblies staged proximate a robotic arm, the selection based upon one or more of the multiple structural features associated with the part to be inspected, engaging the selected NDI probe assembly with the robotic arm, moving the robotic arm from the staging area to an inspection area such that the selected NDI probe assembly engages the part to be inspected proximate one of the structural features of the part that is associated with the selected NDI probe assembly, guiding the NDI probe assembly along the part in a defined path while a transducer associated with the selected NDI probe assembly provides and receives signals associated with NDI, returning the selected NDI probe assembly to the staging area, and repeating the selecting, engaging, moving guiding, and returning steps for at least one more NDI probe assembly staged proximate the robotic arm, each NDI probe assembly associated with at least one different structural feature of the part and communicatively coupled to a corresponding electronic assembly both when the NDI probe assembly is deployed on the robotic arm and when staged proximate the robotic arm.

In still another aspect, a non-destructive inspection (NDI) system is provided that includes a linear track, a carriage operable to move along the linear track, a robotic arm mounted to the carriage, a storage device mounted to the carriage, a plurality of electronic assemblies mounted to the carriage, and a plurality of NDI probe assemblies disposed within the storage device communicatively coupled to a corresponding electrical assembly. Each of the electronic assemblies is operable to provide signals for the operation of specific transducers utilized in NDI. Each NDI probe assembly includes at least one transducer operable for NDI of a component and a mechanical interface to the robotic arm, for NDI of a component having a plurality of structural features. The system is programmed to operate the robotic arm to select, engage and remove one of the NDI probe assemblies from the storage device for NDI of at least one specific structural feature, place the removed NDI probe assembly in a position with respect to the component such that the at least one transducer associated with the NDI probe assembly is proximate a start position for NDI of the at least one structural feature, execute a command to start the NDI, move the removed NDI probe assembly along at least one defined scan path using at least one of the carriage and the robotic arm, and return the removed NDI probe assembly to the storage device upon completion of the NDI of the structural features of the component associated with the removed NDI assembly. The system is further programmed to repeat the operation, placement, execution, movement and returning for each of the NDI probe assemblies within the storage device needed to complete a specific set of NDI tests for a plurality of structural features associated with the component.

The features, functions, and advantages that have been discussed can be achieved independently in various embodiments or may be combined in yet other embodiments further details of which can be seen with reference to the following description and drawings.

DETAILED DESCRIPTION

Figure 1:
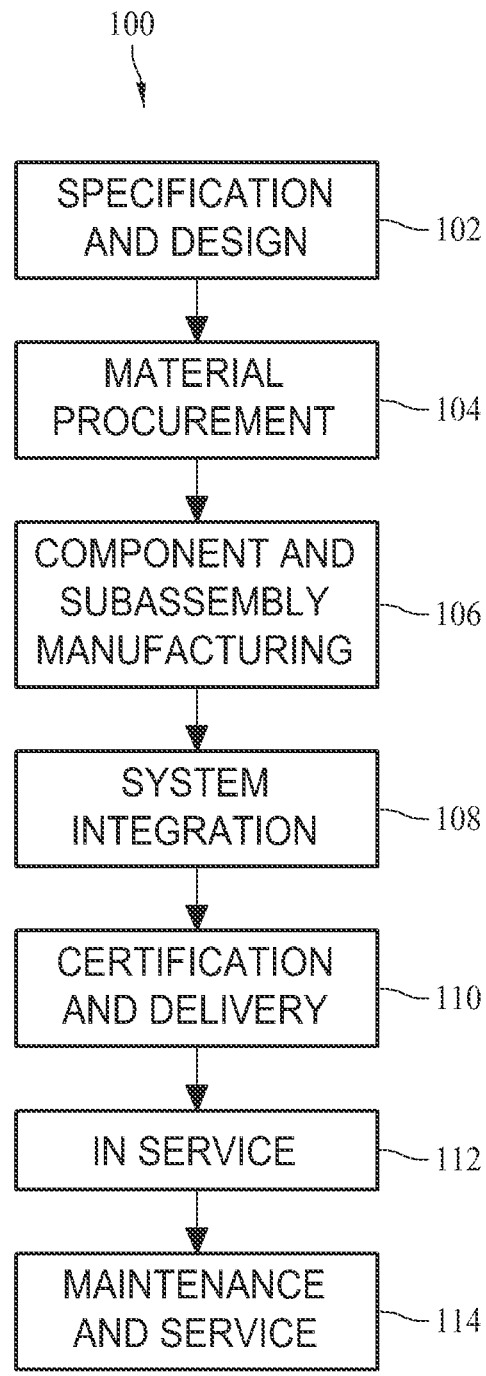
FIG. 1 is a flow diagram of an aircraft production and service methodology.

The described embodiments are directed to a non-destructive inspection (NDI) system that performs NDI of multiple ribs and stringers for an aircraft, though the embodiments should not be construed to be so limited. The described embodiments perform the NDI in a shallow water tank, which is more cost efficient than deep water tank NDI testing.

In an embodiment, the NDI system incorporates a robotic arm and multiple NDI probe assemblies that can be interchanged on the robotic arm which allows for implementation of NDI of composite ribs of different design. More specifically, the programming associated with operation of the robotic arm and the multiple NDI probe assemblies yield good data scans and provides efficient NDI scans for multiple rib configurations. Further, the described NDI system embodiments are (estimated >5x) faster and more reliable than NDI systems currently utilized to inspect similar structures. The NDI process is automated by the embodiments described herein, allowing for a reduction in the number of NDI operators.

To accomplish the above mentioned improvements, the NDI system incorporates multiple NDI probes assemblies for inspection of the various structural features of the various composite parts. Such probe assemblies are incorporated into an automated system for NDI. The NDI system further incorporates a robotic arm that facilitates NDI probe selection, positioning and scanning. The usage of multiple NDI probe assemblies with a single robotic arm device results in reduced cost as multiple NDI systems and/or robotic systems for the probe scanning of the various composite structural parts are not needed.

In one embodiment, technical effects of the methods, systems, and computer-readable media described herein include at least one of: (a) providing a lean and efficient non-destructive inspection system and method for a complex composite part, (b) selecting an NDI probe assembly from a plurality of NDI probe assemblies staged proximate a robotic arm, the selection based upon one or more of the multiple structural features associated with the part to be inspected, (c) engaging the selected NDI probe assembly with the robotic arm, (d) moving the robotic arm from the staging area to an inspection area such that the selected NDI probe assembly engages the part to be inspected proximate one of the structural features of the part that is associated with the selected NDI probe assembly, (e) guiding the NDI probe assembly along the part in a defined path while a transducer associated with the selected NDI probe assembly provides and receives signals associated with NDI, (f) returning the selected NDI probe assembly to the staging area, and (g) repeating the selecting, engaging, moving guiding, and returning steps for at least one more NDI probe assembly staged proximate the robotic arm, each NDI probe assembly associated with at least one different structural feature of the part.

As used herein, an element or step recited in the singular and proceeded with the word "a" or "an" should be understood as not excluding plural elements or steps unless such exclusion is explicitly recited. Furthermore, references to "one embodiment" of the present invention or the "exemplary embodiment" are not intended to be interpreted as excluding the existence of additional embodiments that also incorporate the recited features.

Figure 2:
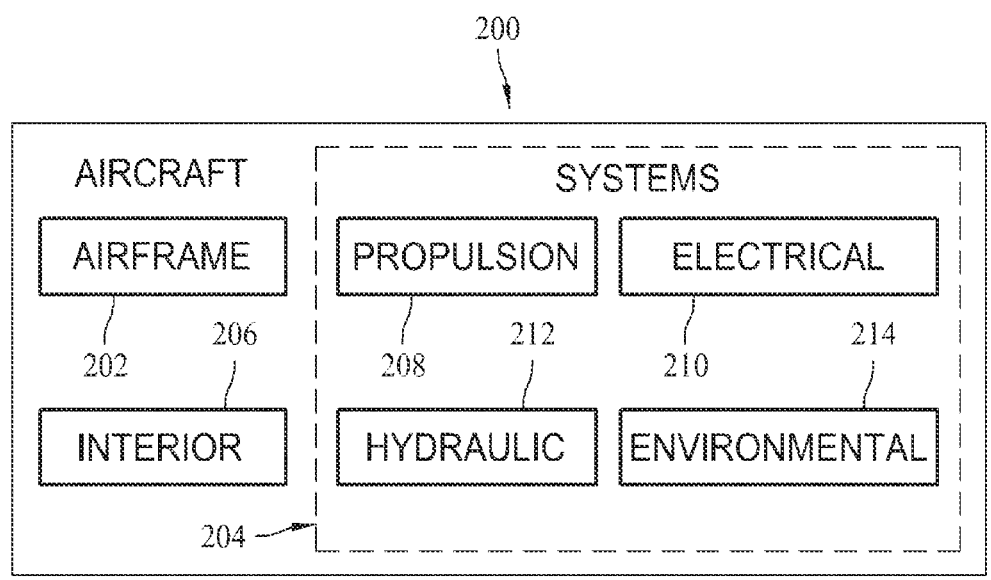
FIG. 2 is a block diagram of an aircraft.

Referring more particularly to the drawings, embodiments of the disclosure may be described in the context of aircraft manufacturing and service method 100 as shown in FIG. 1 and an aircraft 200 as shown in FIG. 2. During pre-production, aircraft manufacturing and service method 100 may include specification and design 102 of aircraft 200 and material procurement 104.

During production, component and subassembly manufacturing 106 and system integration 108 of aircraft 200 takes place. Thereafter, aircraft 200 may go through certification and delivery 110 in order to be placed in service 112. While in service by a customer, aircraft 200 is scheduled for routine maintenance and service 114 (which may also include modification, reconfiguration, refurbishment, and so on).

Each of the processes of aircraft manufacturing and service method 100 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

As shown in FIG. 2, aircraft 200 produced by aircraft manufacturing and service method 100 may include airframe 202 with a plurality of systems 204 and interior 206. Examples of systems 204 include one or more of propulsion system 208, electrical system 210, hydraulic system 212, and environmental system 214. Any number of other systems may be included in this example. Although an aerospace example is shown, the principles of the disclosure may be applied to other industries, such as the automotive industry.

Apparatus and methods embodied herein may be employed during any one or more of the stages of aircraft manufacturing and service method 100. For example, without limitation, components or subassemblies corresponding to component and subassembly manufacturing 106 may be fabricated or manufactured in a manner similar to components or subassemblies produced while aircraft 200 is in service.

Also, one or more apparatus embodiments, method embodiments, or a combination thereof may be utilized during component and subassembly manufacturing 106 and system integration 108, for example, without limitation, by substantially expediting assembly of or reducing the cost of aircraft 200. Similarly, one or more of apparatus embodiments, method embodiments, or a combination thereof may be utilized while aircraft 200 is in service, for example, without limitation, to maintenance and service 114 may be used during system integration 108 and/or maintenance and service 114 to determine whether parts may be connected and/or mated to each other.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited for the particular use contemplated.

Figure 3:
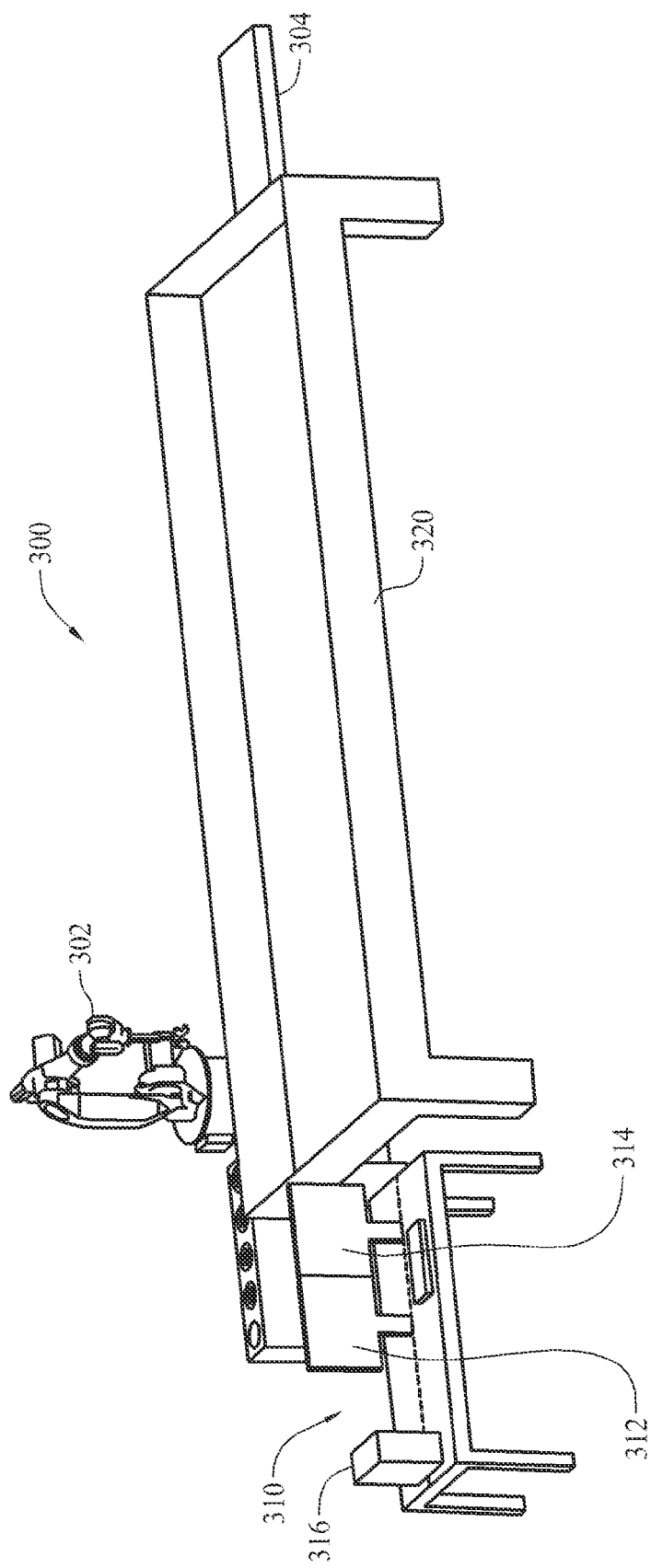
FIG. 3 is a front view depiction of a non-destructive inspection (NDI) system according to one embodiment.
Figure 4:
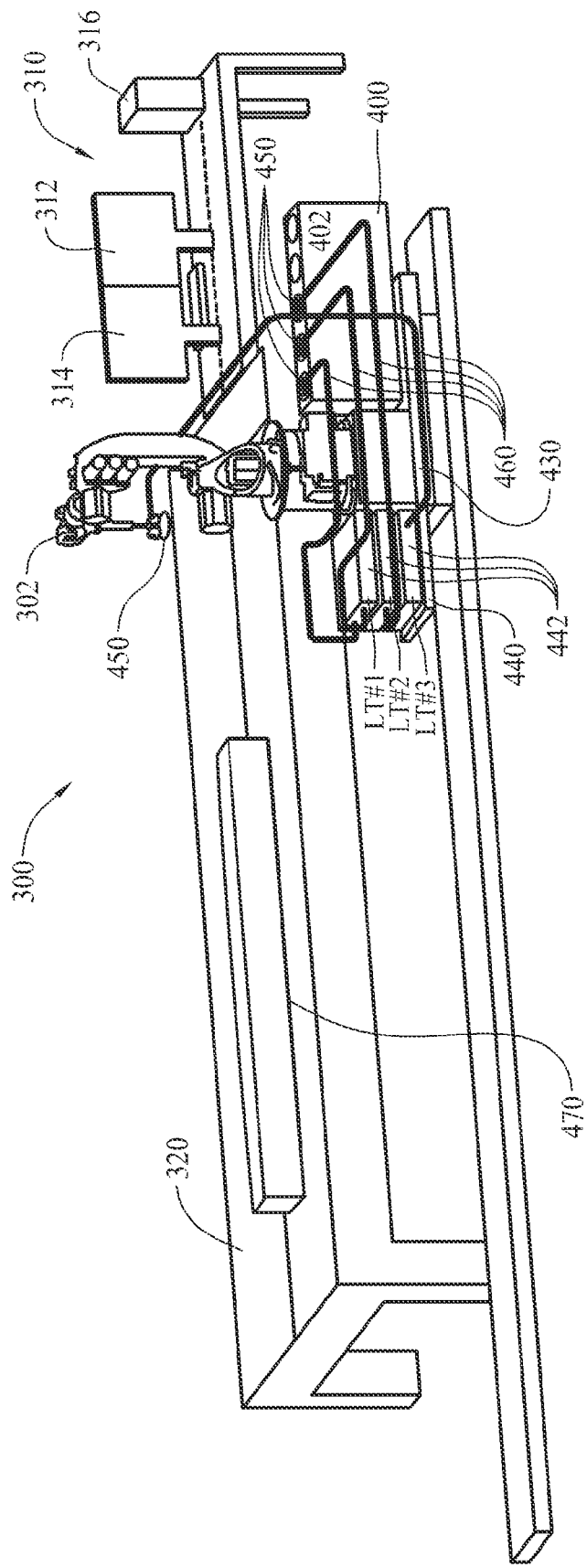
FIG. 4 is a rear view depiction of the NDI system of FIG. 3.

Turning now to FIG. 3, a diagram of a non-destructive inspection (NDI) system 300 is depicted in accordance with an illustrative embodiment. The system 300 shall consist of multiple data acquisition, ultrasonic electronic and robotic mechanical scan sub-systems in combination with corresponding probes and probe holders as well as a part immersion tank arranged as shown in FIGS. 3 and 4. More specifically, NDI system 300 includes a six-axis joint-arm (pedestal) robot 302 movable along a linear rail 304. In the configuration of FIG. 3, incorporation of the linear unit 304 in combination with robot 302 provides a total of seven axes of coordinated motion. As shown in FIG. 3, NDI system 300 includes an operator interface 310 that includes, for example, displays 312, 314 and processing device 316. A shallow water tank 320 is utilized for immersion of the components to be subjected to the NDI tests. As can be understood from FIG. 3, movement of robot 302 along rail 304, and the six axis movement of robot 302 allows for an inspection probe 330 to be moved to any location within shallow water tank 320.

Robot 302 further incorporates an ultrasonic probe assembly changer capability as better seen in the rear view of FIG. 4. Referring to FIG. 4, a probe storage device 400 includes a master side plate 402 that is attached to a face plate 410 of the robot 302. Probe storage device 400 is configured for storage of a plurality of probe assemblies as further described below.

A linear axis carriage 430 provides space for an equipment rack 440 containing electronic units 442 that correspond to the specific ultrasonic units within the individual probe assemblies 450 disposed within probe storage device 400. To address the issues described herein with the connecting, disconnecting, and reconnecting of probe assemblies 450 to their respective supporting electronics units 442, a series of cables 460 are incorporated into NDI system 300 that allow for the semi-permanent attachment between the electronic units 442 and respective NDI probe assemblies 450. In use, the cables 460 are routed and maintained in positions that allow for the robot 302 to extract, utilize, and replace an individual probe assembly 450 with respect to probe storage device 400 while maintaining the electrical interconnection between the electronic units 442 and respective NDI probe assemblies 450. One of cables 460 is shown in FIG. 460 as being connected to an NDI probe assembly 450 that is deployed on the robot 302.

In an embodiment, each probe assembly 450 consists of one or more ultrasonic inspection probes, the associated probe holder and a tool that provides a mechanical interface between the robot 302 and the probe assembly 450. In the NDI of a lower inside radius of an aircraft stringer, for example, multiple NDI probe assemblies 450 may be utilized. In one NDI probe assembly 450, for example, an outside magnetic guidance fixture is provided as well as a holder for the ultrasonic transducers. The outside guidance fixture is configured for the mechanical placement of the corresponding transducer(s) in specific locations with respect to a component being inspected by system 300. Specifically, the outside magnetic guidance fixture is operable, via the robotic arm 302 to engage a component 470 upon which an NDI is to be performed. As such, the multiple probe assemblies 450 correspond to and incorporate the various mechanical features necessary to place the various transducers in positions that allow for the complete NDI of a component or part.

Cables connecting the ultrasonic inspection probes (e.g., pulser-receiver units) and the corresponding electronic units 442 are deployed within a cable track sufficient to enable all required electrical interconnects between the linear unit of robot 302 and the fixed equipment stand of operator interface 310. As an example, a cable track generally contains a 110 volt AC power line, and an Ethernet data transfer cable.

Operation of NDI system 300 requires an operator to enter the working space of the robot 302. In one embodiment, a railing system and light screen based robot guarding system is incorporated into NDI system 300 that deactivates the power to the robot 302 when the operator enters the work space.

NDI system 300 utilizes a robotic motion control program that can be converted into executable scan programs by adding point coordinates using a teach pendant. The basic motion control program is designed to start at a safe "home" position, select an NDI probe assembly 450, do a series of approximately straight line scans, return the NDI probe assembly 450, and return to home. In embodiments, the home position is different for each of the parts that are tested with the NDI system 300. This is necessary so since the scanning of the parts with NDI system 300 requires a different program be executed to inspect each of the parts. Also, each of the probes will require a different scanning program due to the mechanical configuration differences. In embodiments of the scanning programs, safety features are linked into the scanning software to prevent collisions between the probe and robot combination and one or more of the part being inspected, the tooling fixtures, and the shallow water tank 320.

Figure 5:
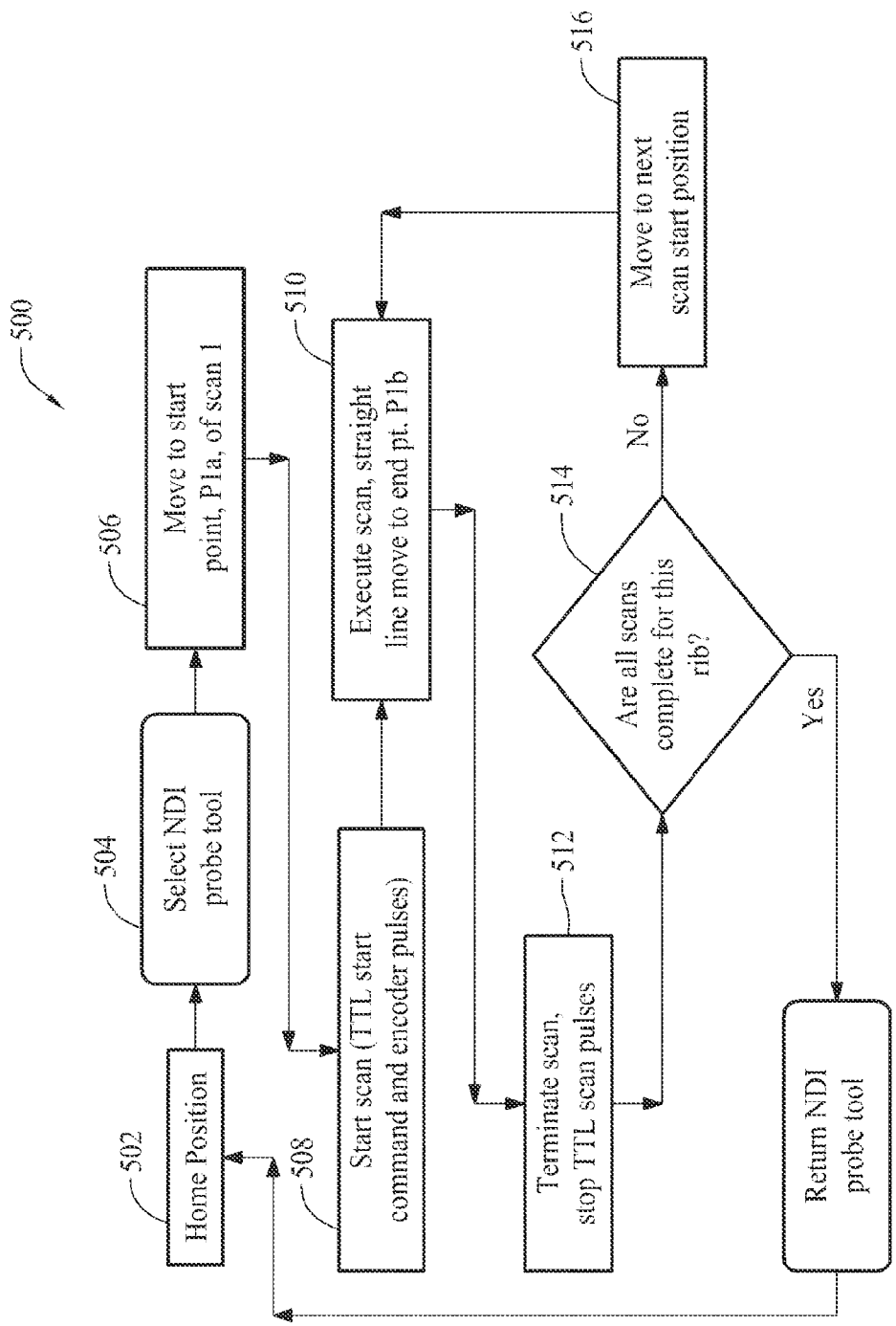
FIG. 5 is a flowchart illustrating robotic motion control program actions for the NDI of a part using the system of FIGS. 3 and 4.

FIG. 5 is a flowchart 500 illustrating robotic motion control program actions for the NDI of a part, in this example a rib, using the system 300 described herein. The robot 302 is programmed to start by moving 502 the effector end to a home position. An NDI probe assembly 450 is selected 504, based on the relevant portion of the part that is to be inspected. Selection of the NDI probe assembly 450 includes moving the arm of the robot 302 to the location where the relevant NDI probe assembly can be extracted from probe storage device 400. Based on the program being executed, the extracted NDI probe assembly 450 is moved 506 to starting point P1a of scan 1. As understood, there is an interpolation between a position of the robot, its arm, and the transducer of the probe assembly 450 that is attached to the robot.

The scan is started 508 as the system 300 issues a TTL scan start pulse and begins output of position pulses. The scan is executed 508, for example, by moving the effector end (the transducer within the probe) in a straight line from point P1a to end point P1b. Generally, movement is approximately along an axis. As the effector end reaches end point P1b, output of position pulses is terminated 512 and a TTL scan stop pulse is issued. The end effector is moved upwards to a clearance position, generally along a positive Z axis, and if the scan is not complete 514, the probe assembly, and therefore the transducer, are moved 516 to the starting position of the next scan, for example, start point P2a of scan 2. The remaining scans are executed, as shown in flowchart 500 until all scans associated with the particular NDI probe assembly 450 are complete 514, at which point the NDI probe assembly 450 is returned 518 to probe storage device 400, and the robot arm is returned to the home position.

In one embodiment, and relevant to a specific set of composite components to be inspected, ultrasonic data is generated, with the various probe assemblies 450, in the following order with start scan and end of scan pulses for each data segment: N segments of upper radius and cap data for hat stiffeners 1 through N, N segments of lower radius and side data for hat stiffeners 1 through N, N segments of inner radius data for hat stiffeners 1 through N, M segments of web data for the composite rib, and stitched scans of the web.

Figure 6:
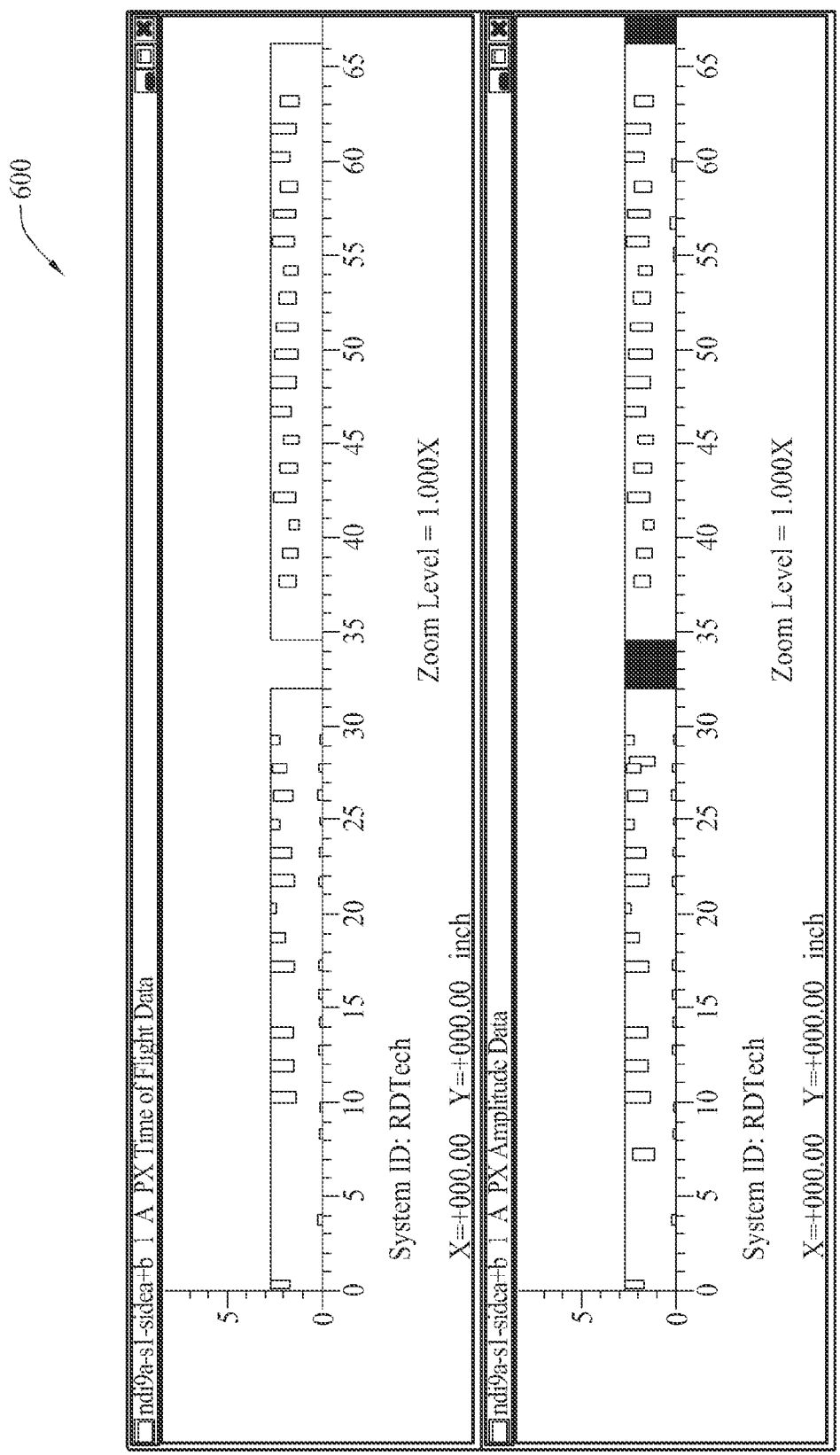
FIG. 6 includes plots of upper radius and cap data for hat stiffeners.
Figure 7:
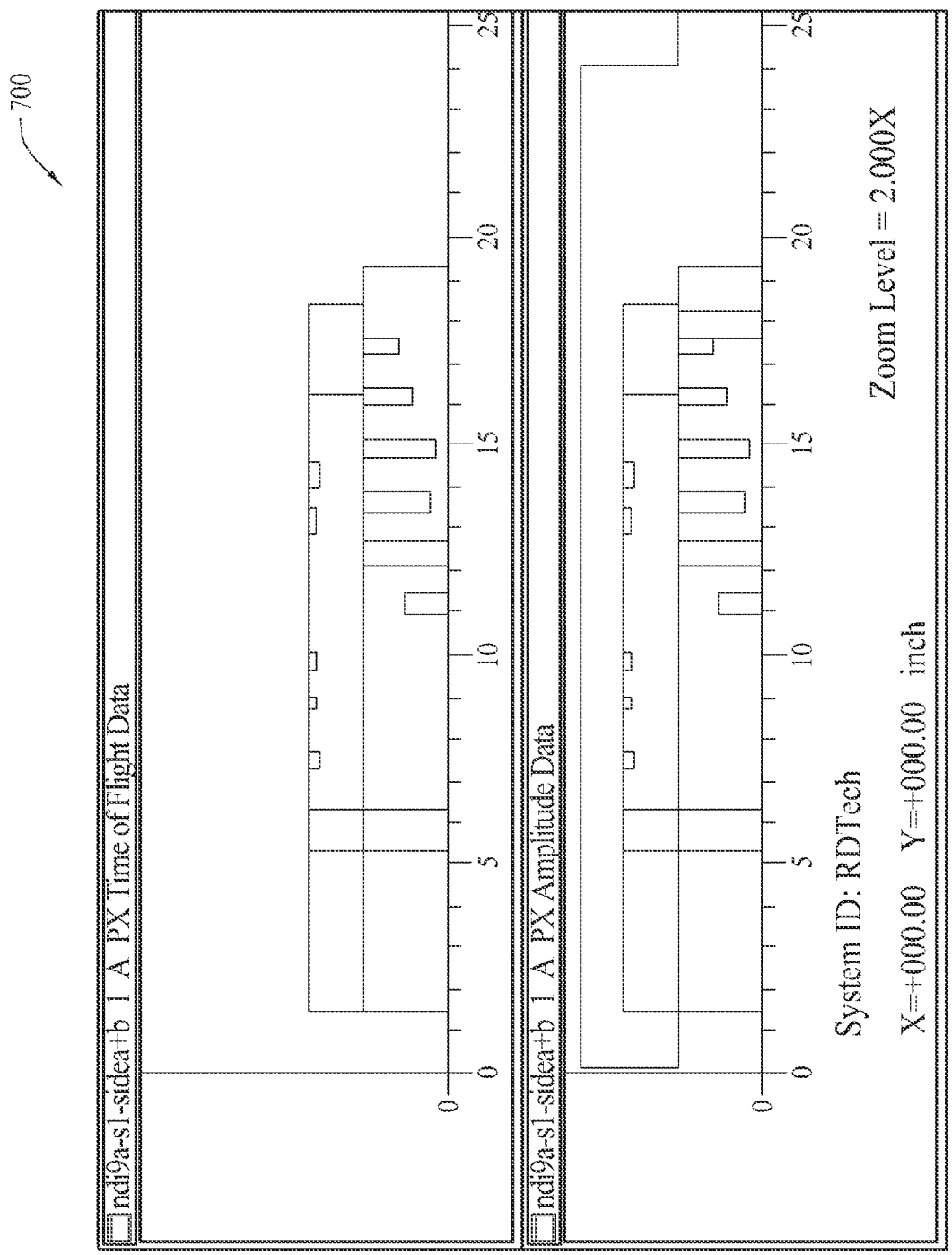
FIG. 7 includes plots of lower radius and side data for hat stiffeners.
Figure 8:
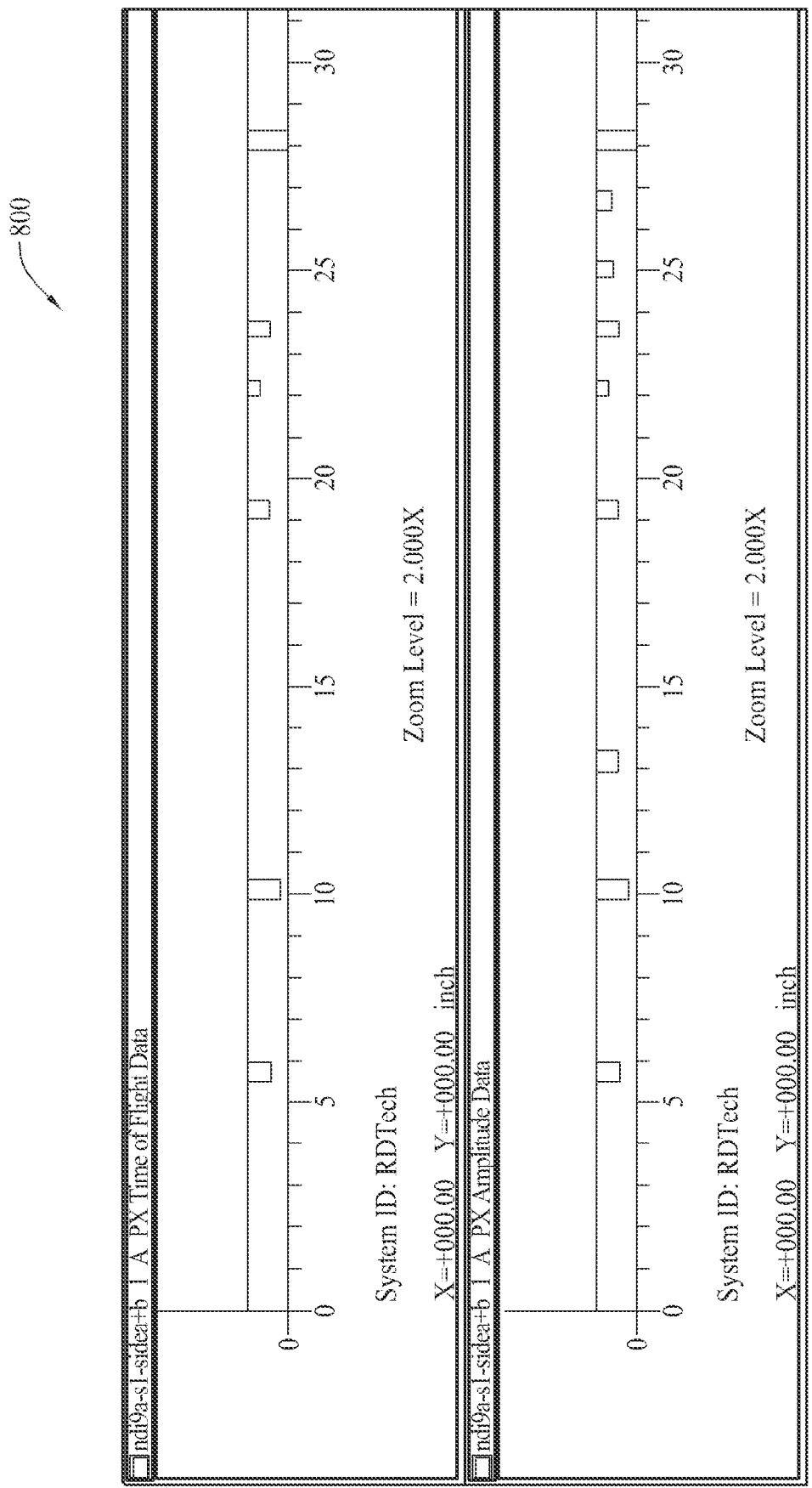
FIG. 8 includes plots of inner radius data for hat stiffeners.

The data acquisition software operating in one embodiment of system 300 displays the data arranged as follows: N segments each containing aligned upper radius and cap, lower radius and side, and inner radius data. More particularly, the data is displayed as shown in FIGS. 6 through 8, where FIG. 6 includes plots 600 of upper radius and cap data for hat stiffeners, FIG. 7 includes plots 700 of lower radius and side data for hat stiffeners, and FIG. 8 includes plots 800 of inner radius data for hat stiffeners. Plots 600, 700, and 800 have the stringer data shown individually per transducer shoe. For NDI analysis process flow, it is desired to have the data files stitched together and displayed in one image per rib.

Figure 9A:
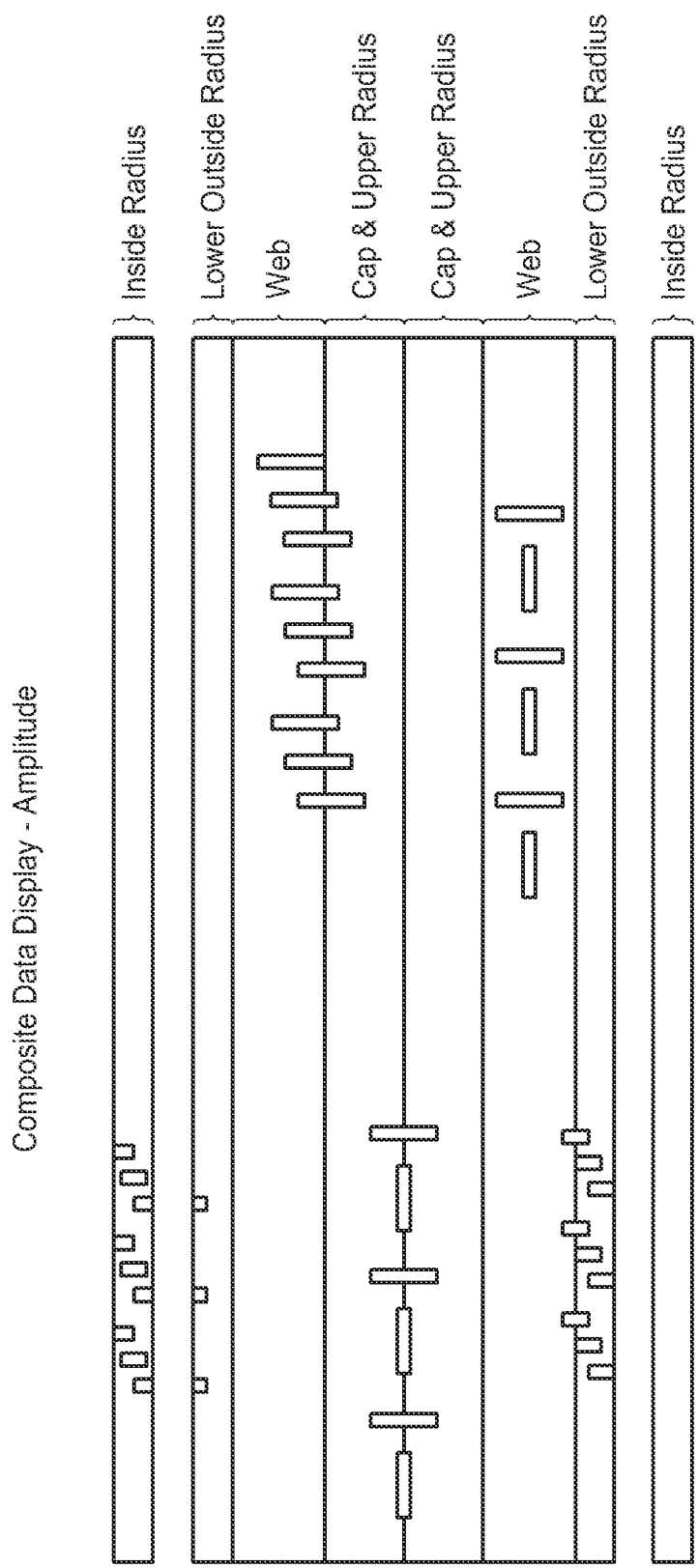
FIG. 9A illustrates composite data from NDI transducers in the form of amplitude data.
Figure 9B:
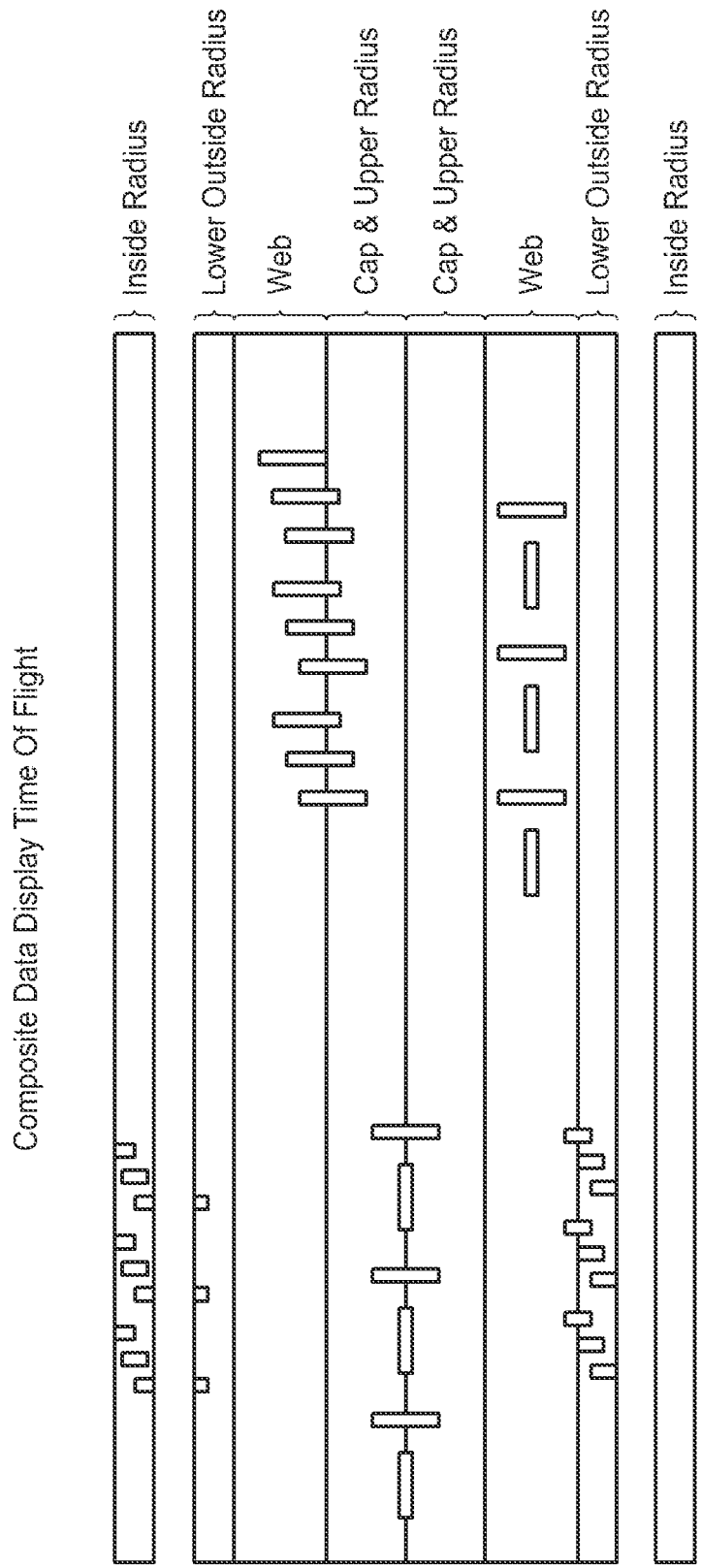
FIG. 9B illustrates composite data from NDI transducers in the form of time of flight data.

The data after it has been acquired for all the probes for a stringer shall display the data as a composite image. FIGS. 9A and 9B have both the amplitude and time of flight images for the data files per ultrasonic gate as FIGS. 9A and 9B include plots 900 and 910 respectively illustrate composite data from the transducers in the form of amplitude data and time of flight data.

Figure 10:
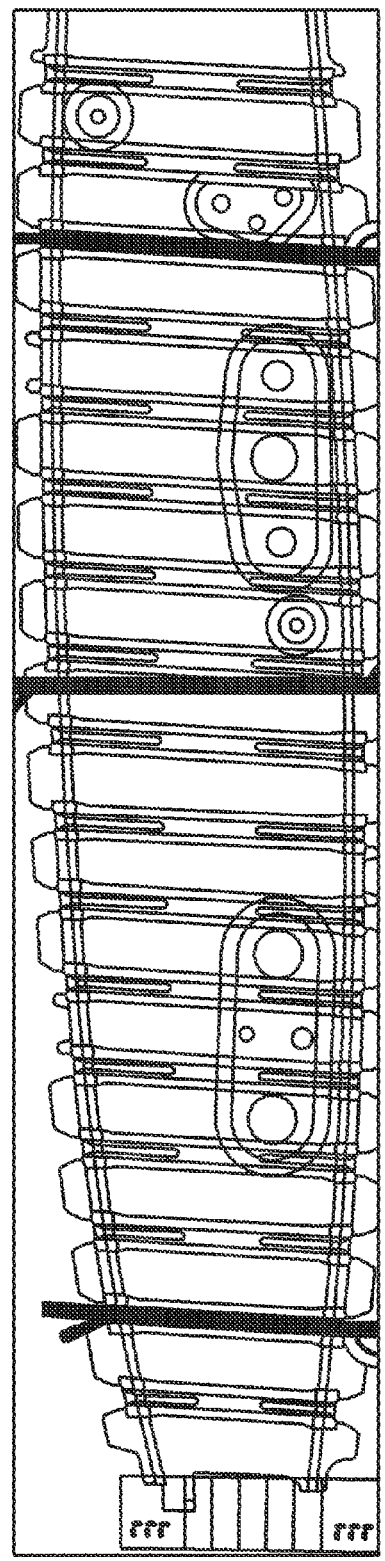
FIG. 10 is an image of amplitude data as stitched together by the system of FIGS. 3 and 4.

In one embodiment, the NDI data scans for the composite rib are stitched together into one image where amplitude and time of flight data are displayed. FIG. 10 is an image 1000 of the amplitude data as stitched together by system 300.

Figure 11:
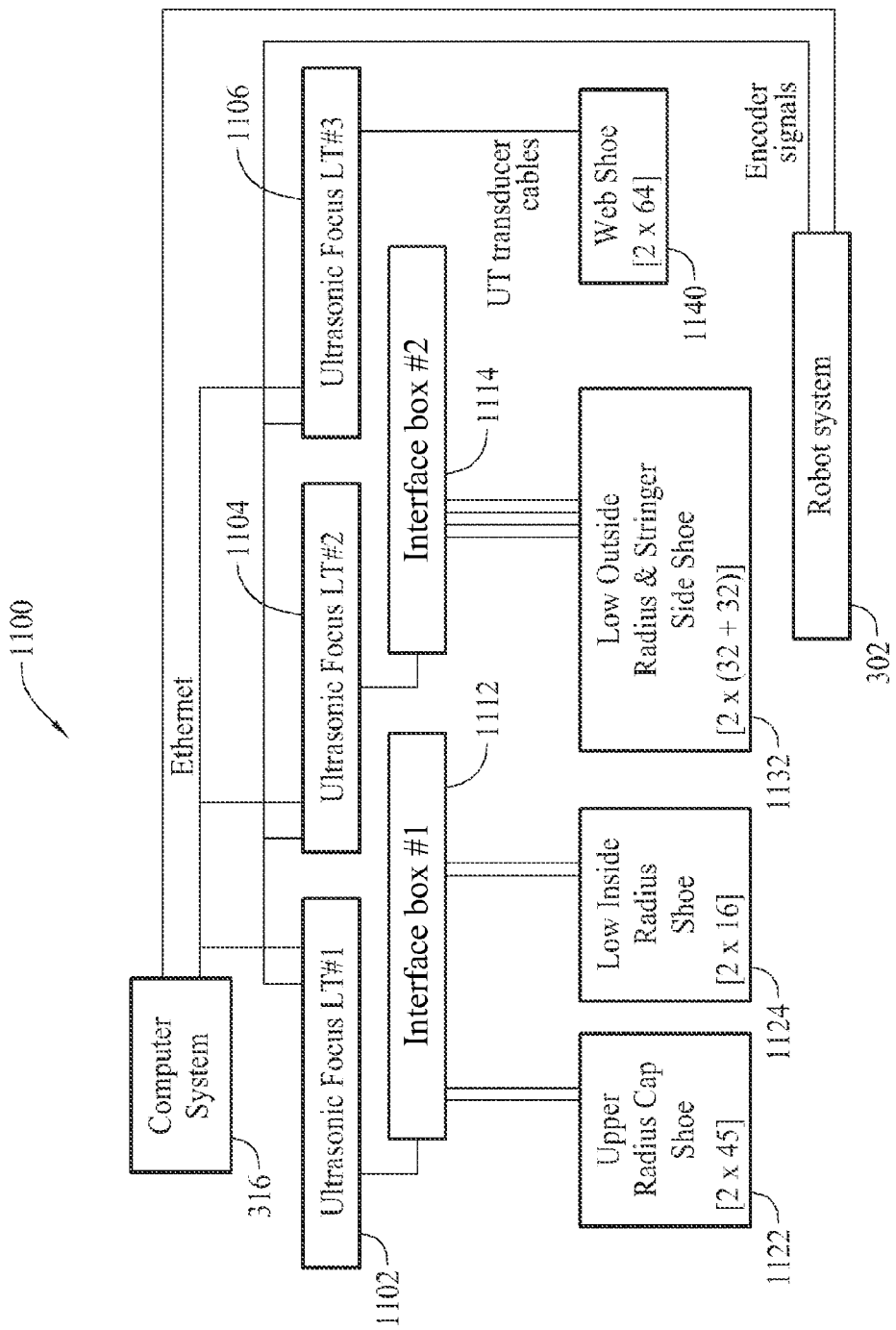
FIG. 11 is a block diagram of one embodiment of an ultrasonic subsystem interface for the system of FIGS. 3 and 4.

FIG. 11 is a block diagram of one embodiment of a ultrasonic subsystem interface 1100 for system 300. In the illustrated embodiment, subsystem interface 1100, which is sometimes referred to as an electronic pulser-receiver system, includes three linear transducer units 1102, 1104, 1106 that are coupled to the computer 316, also providing encoder signals to robot 302. In a specific embodiment, transducer units 1102, 1104, and 1106 are Olympus NDT Focus linear transducer units, though NDI systems could also be utilized in addition or in combination with those shown in FIG. 11. As shown in FIG. 11, transducer unit 1102 is coupled to an interface box 1112, which provides an interface between transducer unit 1102 and the transducers therein, particularly an upper radius cap shoe transducer element 1122 and a low inside radius shoe transducer element 1124. Transducer unit 1104 is coupled to an interface box 1114, which provides an interface between transducer unit 1104 and the transducers therein, particularly a low outside radius and stringer side shoe transducer element 1132. Transducer unit 1106 is directly coupled to a web shoe transducer 1140.

Figure 12:
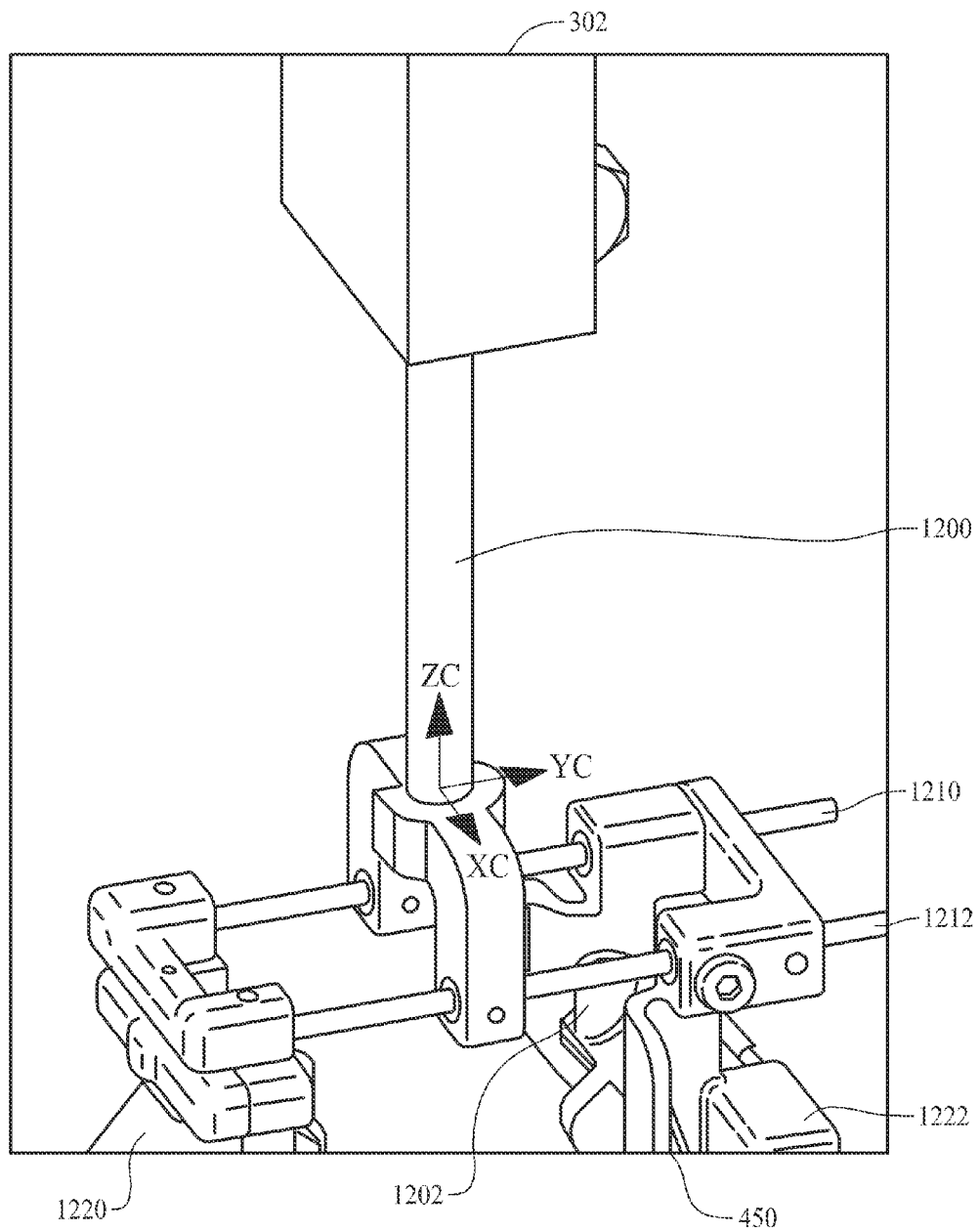
FIG. 12 is a view of a probe assembly.

FIG. 12 is a view of a probe assembly 450. In operation, a probe holder 1200 is attached to the robot 302. The robot 302 is programmed to engage the appropriate probe assembly 450 such that it is extracted from probe storage device 400 and placed into the shallow water tank such that a transducer 1202 mounted in probe assembly 450 is proximate the starting point referred to above. Further, probe assembly 450 includes, in one embodiment, one or more guide bars 1210, 1212, are utilized to mechanically connect probe assembly halves 1220 and 1222 of probe assembly 450, with probe assembly half 1222 being movable with respect to probe assembly half 1220. In one embodiment, magnets are utilized in probe assembly halves 1220 and 1222, both in an attracting mode and in a repulsion mode, to move the probe assembly half 1222 such that probe assembly 450 properly engages the portion of the composite part that is to undergo NDI testing.

Figure 13:
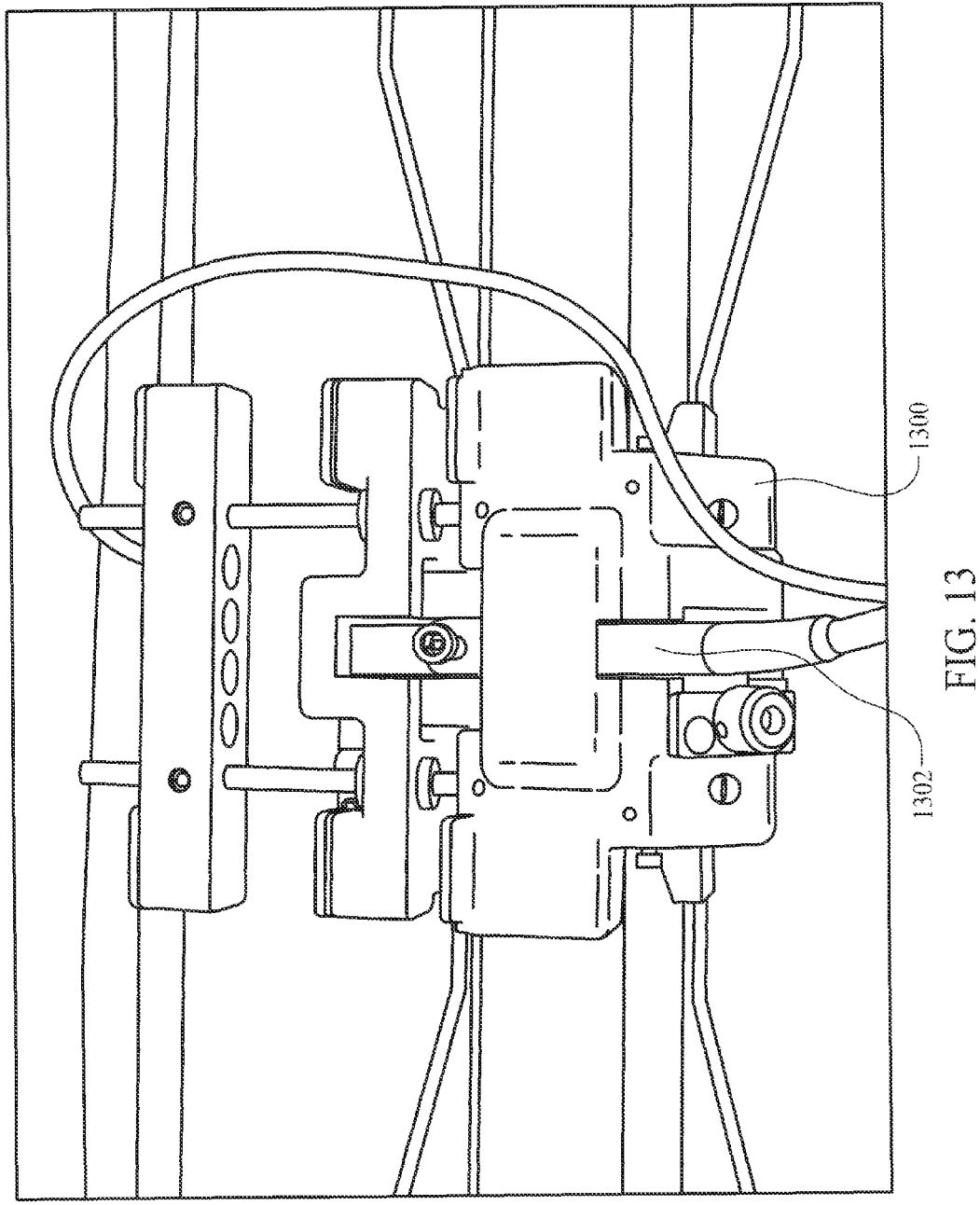
FIG. 13 is a view of an upper radius and cap probe assembly.
Figure 14:
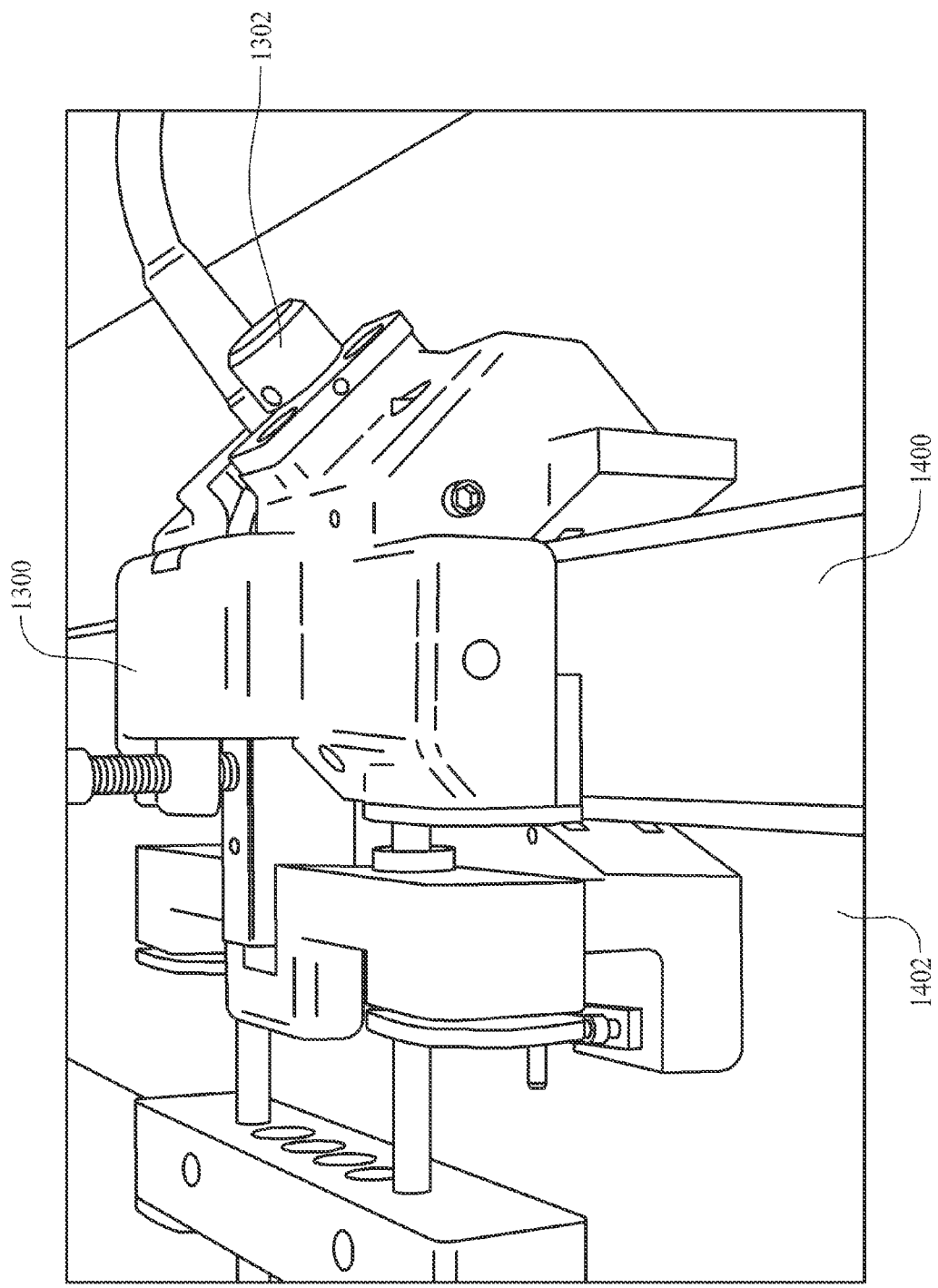
FIG. 14 is an alternate view of the upper radius and cap probe assembly of FIG. 13.

FIG. 13 is a view of a probe assembly, including transducer 1302. Probe assembly 1300 is referred to an upper radius and cap probe and is configured for the testing of a top cap 1400 in composite part 1402, as shown in FIG. 14. For clarity, the mechanical interface between robot 302 and probe assembly 1300 is not shown.

Figure 15:
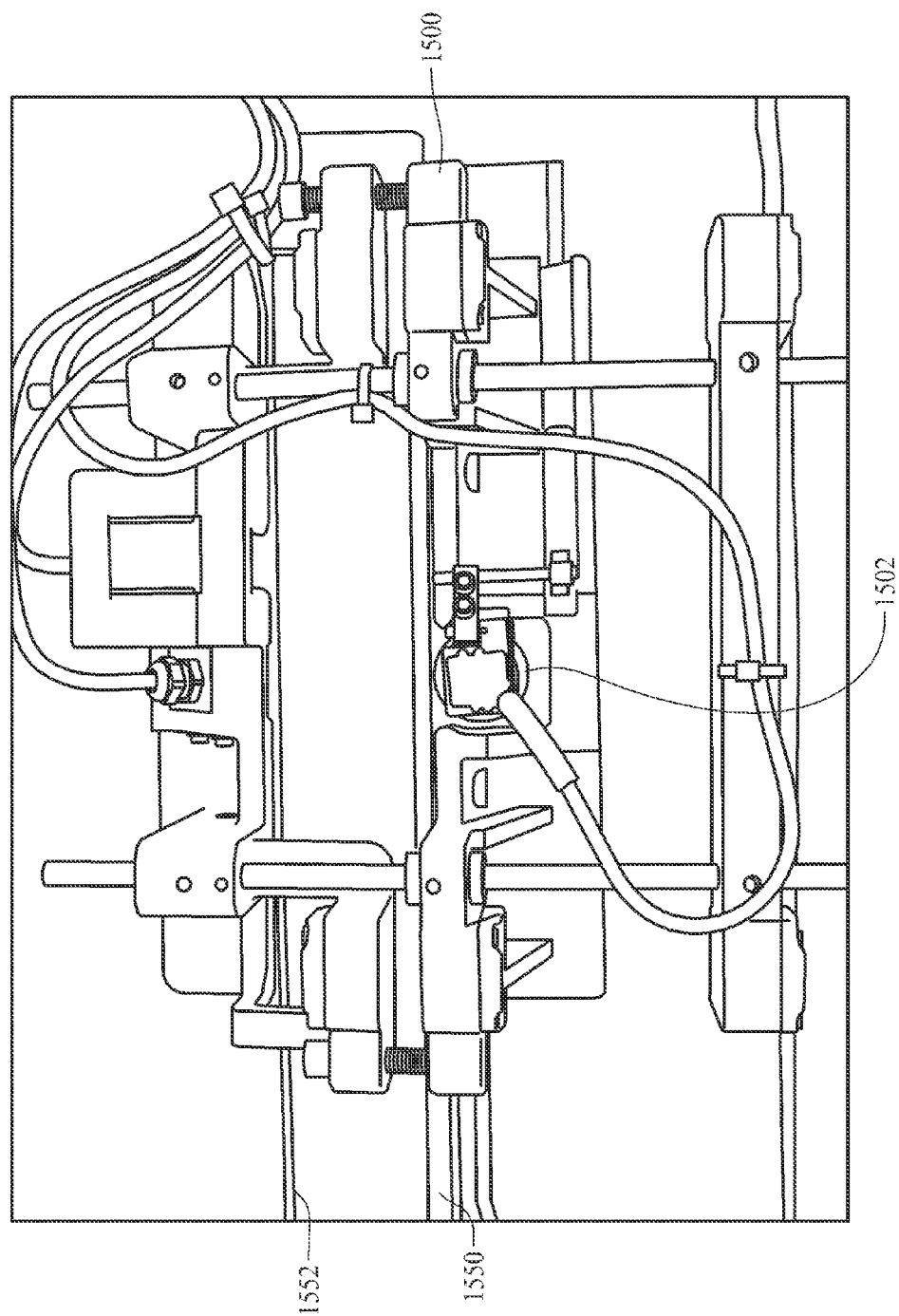
FIG. 15 is a view of a lower radius and side probe holder assembly.
Figure 16:
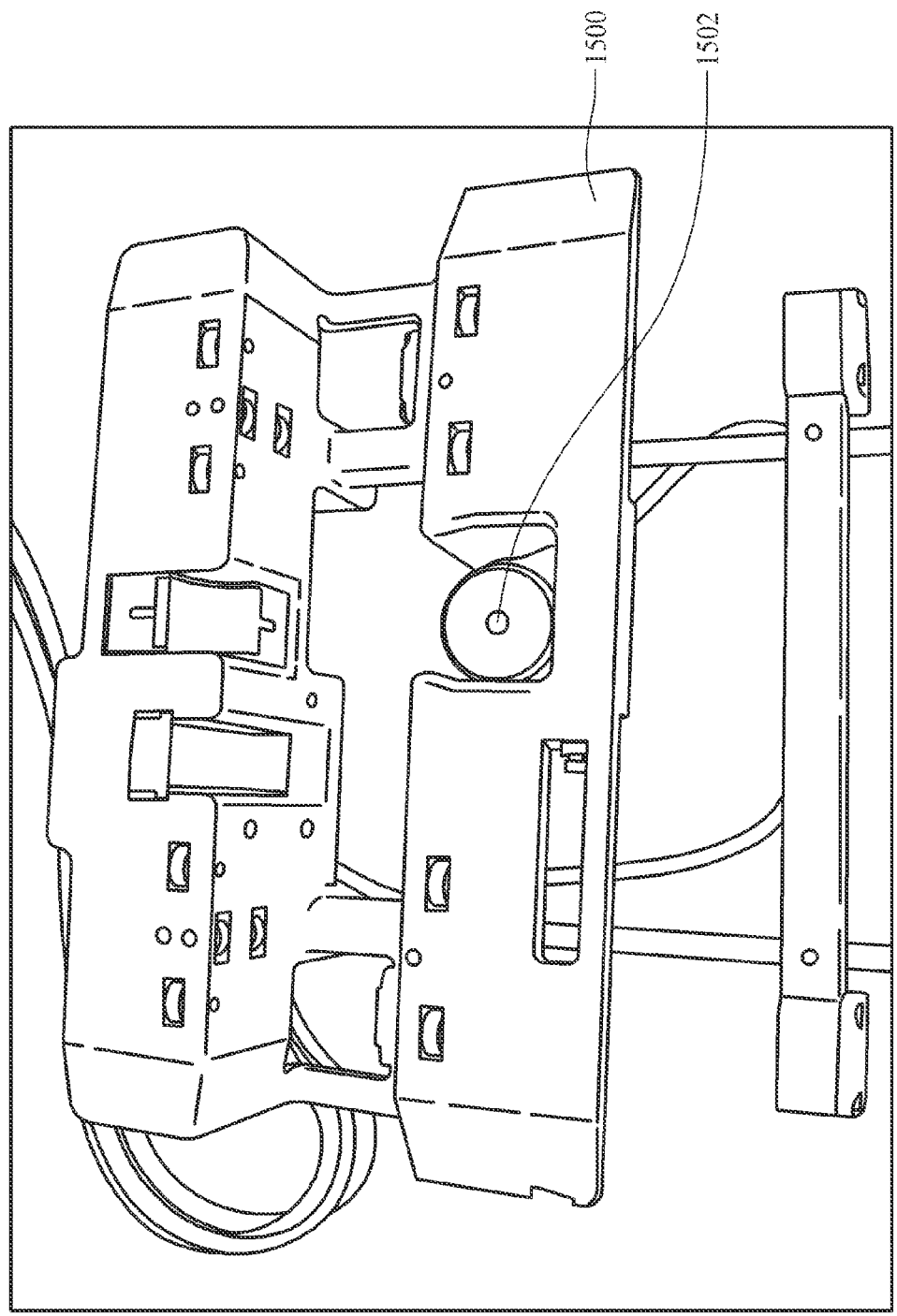
FIG. 16 is an alternate view of the lower radius and side probe holder assembly of FIG. 15.

The probe assembly 1500 of FIG. 15 illustrates an alternative probe assembly configuration. More particularly, probe assembly 1500 incorporates a transducer 1502 positioned for testing of a side wall 1550 of a top cap 1552. Probe assembly 1500 is sometimes referred to as a lower radius and side probe holder assembly. FIG. 16 is a bottom view of probe assembly 1500 further illustrating transducer 1502. Again for clarity, the mechanical interface between robot 302 and probe assembly 1500 is not shown.

Figure 17:
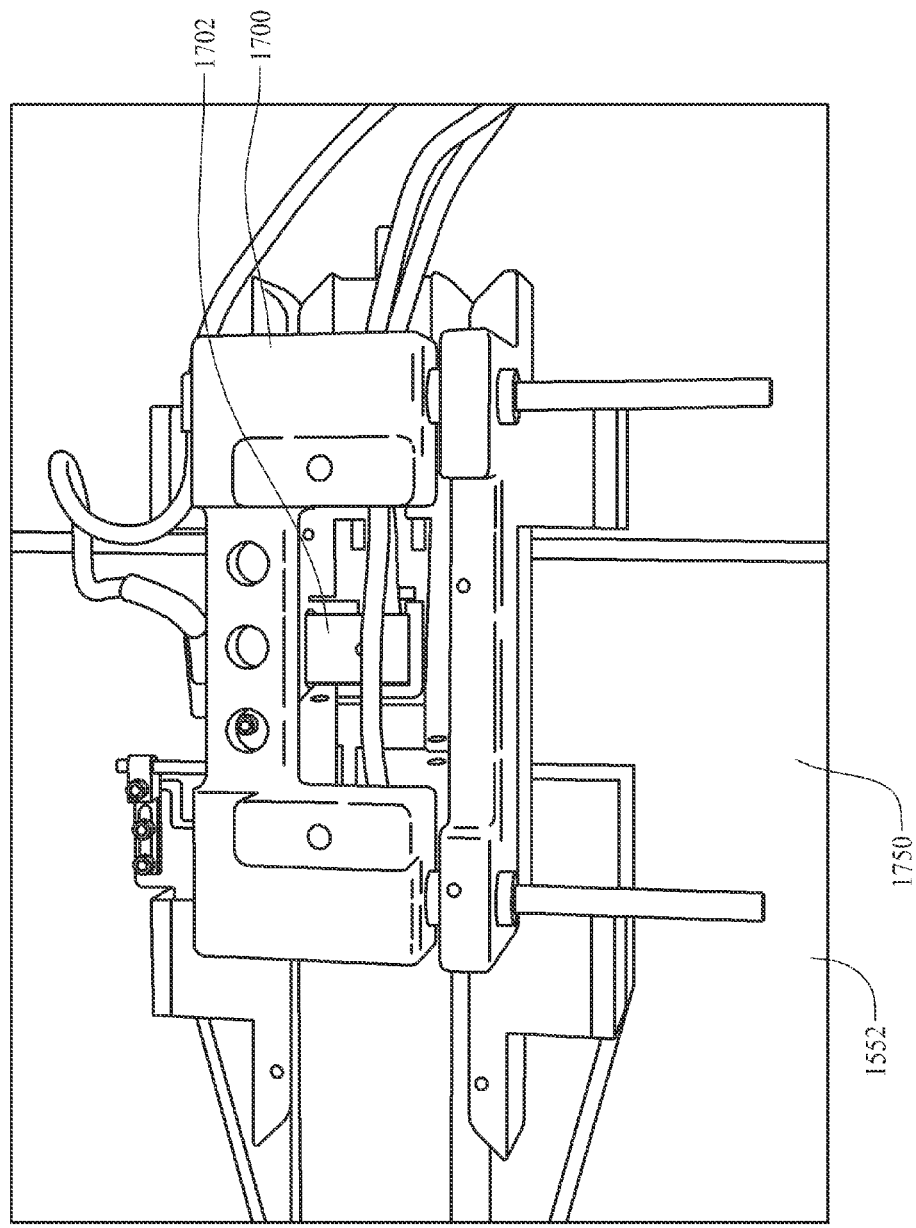
FIG. 17 illustrates an inner radius probe holder assembly.

The probe assembly 1700 of FIG. 17 illustrates an alternative probe assembly configuration. More particularly, probe assembly 1700 incorporates a transducer 1702 positioned for testing of an inner radius 1750, for example of top cap 1552. Probe assembly 1700 is sometimes referred to as an inner radius probe holder assembly. The mechanical interface between robot 302 and probe assembly 1700 is not shown.

In use, probe assemblies of the type described herein are placed within the probe storage device 400 which is a portion of the linear unit of the robot 302. With such a configuration, the three example probe assemblies described with respect to FIG. 13-17, and specifically the transducers for each, can be directly and permanently cabled to the electronic units associated with the individual transducers (e.g., ultrasonic arrays) for ease of use as described above with respect to FIGS. 4 and 11. Specifically, when the robot has completed the use of one probe assembly, deposits it into the probe storage device 400, and selects another probe assembly for use, a user does not have to disconnect cabling from the first to use with the second. The pulser-receivers of each probe assembly 450 are connected through the cable track to the data acquisition computer 316 to enable transfer of scan data.

Figure 18:
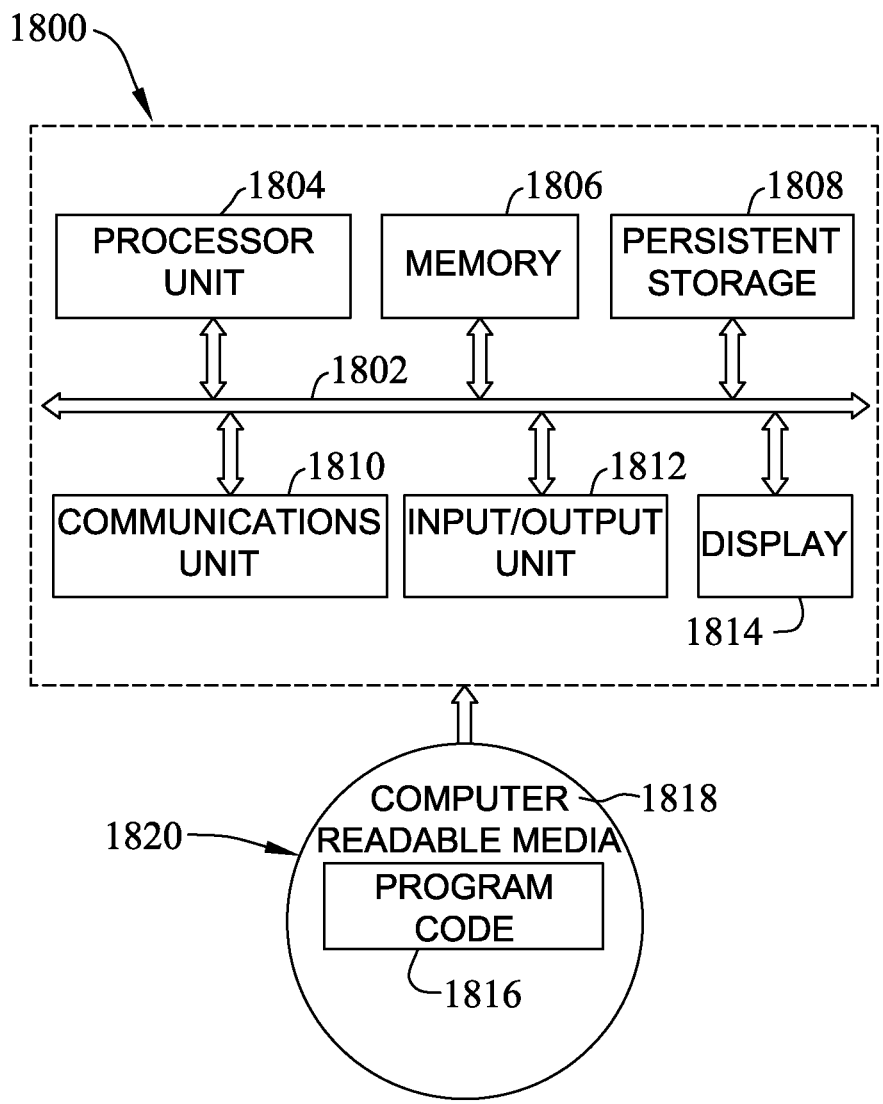
FIG. 18 is a diagram of a data processing system.

Computer 316 and displays 312 and 314 are further illustrated in FIG. 18, which is one example of a data processing system 1800 includes communications fabric 1802, which provides communications between processor unit 1804, memory 1806, persistent storage 1808, communications unit 1810, input/output (I/O) unit 1812, and display 1814. Communication unit 1810 provides an interface to robot 302 and the various NDI probe assemblies 450.

Processor unit 1804 serves to execute instructions for software that may be loaded into memory 1806. Processor unit 1804 may be a set of one or more processors or may be a multi-processor core, depending on the particular implementation. Further, processor unit 1804 may be implemented using one or more heterogeneous processor systems in which a main processor is present with secondary processors on a single chip. As another illustrative example, processor unit 1804 may be a symmetric multi-processor system containing multiple processors of the same type.

Memory 1806 and persistent storage 1808 are examples of storage devices. A storage device is any piece of hardware that is capable of storing information either on a temporary basis and/or a permanent basis. Memory 1806, in these examples, may be, for example, without limitation, a random access memory or any other suitable volatile or non-volatile storage device. Persistent storage 1808 may take various forms depending on the particular implementation. For example, without limitation, persistent storage 1808 may contain one or more components or devices. For example, persistent storage 1808 may be a hard drive, a flash memory, a rewritable optical disk, a rewritable magnetic tape, or some combination of the above. The media used by persistent storage 1808 also may be removable. For example, without limitation, a removable hard drive may be used for persistent storage 1808.

Communications unit 1810, in these examples, provides for communications with other data processing systems or devices. In these examples, communications unit 1810 is a network interface card. Communications unit 1810 may provide communications through the use of either or both physical and wireless communication links.

Input/output unit 1812 allows for input and output of data with other devices that may be connected to data processing system 1800. For example, without limitation, input/output unit 1812 may provide a connection for user input through a keyboard and mouse. Further, input/output unit 1812 may send output to a printer. Display 1814 provides a mechanism to display information to a user.

Instructions for the operating system and applications or programs are located on persistent storage 1808. These instructions may be loaded into memory 1806 for execution by processor unit 1804. The processes of the different embodiments may be performed by processor unit 1804 using computer implemented instructions, which may be located in a memory, such as memory 1806. These instructions are referred to as program code, computer usable program code, or computer readable program code that may be read and executed by a processor in processor unit 1804. The program code in the different embodiments may be embodied on different physical or tangible computer readable media, such as memory 1806 or persistent storage 1808.

Program code 1816 is located in a functional form on computer readable media 1818 that is selectively removable and may be loaded onto or transferred to data processing system 1800 for execution by processor unit 1804. Program code 1816 and computer readable media 1818 form computer program product 1820 in these examples. In one example, computer readable media 1818 may be in a tangible form, such as, for example, an optical or magnetic disc that is inserted or placed into a drive or other device that is part of persistent storage 1808 for transfer onto a storage device, such as a hard drive that is part of persistent storage 1808. In a tangible form, computer readable media 1818 also may take the form of a persistent storage, such as a hard drive, a thumb drive, or a flash memory that is connected to data processing system 1800. The tangible form of computer readable media 1818 is also referred to as computer recordable storage media. In some instances, computer readable media 1818 may not be removable.

Alternatively, program code 1816 may be transferred to data processing system 1800 from computer readable media 1818 through a communications link to communications unit 1810 and/or through a connection to input/output unit 1812. The communications link and/or the connection may be physical or wireless in the illustrative examples. The computer readable media also may take the form of non-tangible media, such as communications links or wireless transmissions containing the program code.

In some illustrative embodiments, program code 1816 may be downloaded over a network to persistent storage 1808 from another device or data processing system for use within data processing system 1800. For instance, program code stored in a computer readable storage medium in a server data processing system may be downloaded over a network from the server to data processing system 1800. The data processing system providing program code 1816 may be a server computer, a client computer, or some other device capable of storing and transmitting program code 1816.

The different components illustrated for data processing system 1800 are not meant to provide architectural limitations to the manner in which different embodiments may be implemented. The different illustrative embodiments may be implemented in a data processing system including components in addition to or in place of those illustrated for data processing system 1800. Other components shown in FIG. 18 can be varied from the illustrative examples shown.

As one example, a storage device in data processing system 1800 is any hardware apparatus that may store data. Memory 1806, persistent storage 1808 and computer readable media 1818 are examples of storage devices in a tangible form.

In another example, a bus system may be used to implement communications fabric 1802 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, without limitation, memory 1806 or a cache such as that found in an interface and memory controller hub that may be present in communications fabric 1802.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for non-destructive inspection (NDI) of a part that incorporates multiple structural features, said method comprising:

selecting an NDI probe assembly from a plurality of NDI probe assemblies staged proximate a robotic arm, the selection based upon one or more of the multiple structural features associated with the part to be inspected;

disposing the plurality of NDI probe assemblies proximate a storage device proximate the robotic arm;

engaging the selected NDI probe assembly with the robotic arm;

moving the robotic arm from the staging area to an inspection area such that the selected NDI probe assembly engages the part to be inspected proximate one of the structural features of the part that is associated with the selected NDI probe assembly;

guiding the NDI probe assembly along the part in a defined path while a transducer associated with the selected NDI probe assembly provides and receives signals associated with NDI;

returning the selected NDI probe assembly to the staging area; and repeating the selecting, engaging, moving, guiding, and returning steps for at least one more NDI probe assembly staged proximate the robotic arm, each NDI probe assembly associated with at least one different structural feature of the part and communicatively coupled to a corresponding electronic assembly both when the NDI probe assembly is deployed on the robotic arm and when staged proximate the robotic arm.

2. The method according to claim 1 further comprising moving the robotic arm along a linear guide proximate the part.

3. The method according to claim 2 wherein the storage device mechanically coupled to the robotic arm for movement along the linear track.

4. The method according to claim 1 wherein moving the robotic arm from the staging area to an inspection area comprises moving the selected NDI probe assembly into a position within a water tank, the part to be inspected disposed within the water tank.

5. The method according to claim 1 wherein guiding the NDI probe assembly along the part in a defined path comprises at least one of:
    moving the robotic arm along a linear track proximate the part undergoing the NDI; and
    moving a six-axis joint arm pedestal associated with the robotic arm.

6. The method according to claim 5 wherein moving the robotic arm from the staging area to an inspection area further comprises engaging the part to be inspected with the guidance fixture such that a transducer within the guidance fixture is properly placed proximate the part for an initial NDI scan.

7. The method according to claim 1 wherein engaging the selected NDI probe assembly with the robotic arm comprises mechanically engaging a guidance fixture within which at least one transducer is mounted.

8. A non-destructive inspection (NDI) system comprising:
    a linear track comprising a carriage operable to move along said linear track;
    a robotic arm mounted to said carriage;
    a storage device mounted to said carriage;
    a plurality of electronic assemblies mounted to said carriage, each of said electronic assemblies operable to provide signals for the operation of specific transducers utilized in NDI; and
    a plurality of NDI probe assemblies disposed within said storage device communicatively coupled to a corresponding said electrical assembly, each NDI probe assembly comprising at least one transducer operable for NDI of a component and a mechanical interface to said robotic arm, for NDI of a component having a plurality of structural features, said system programmed to:
    operate said robotic arm to select, engage and remove one of said NDI probe assemblies from said storage device for NDI of at least one specific structural feature,
    place the removed NDI probe assembly in a position with respect to the component such that the at least one transducer associated with the said NDI probe assembly is proximate a start position for NDI of the at least one structural feature;
    execute a command to start the NDI;
    move the removed NDI probe assembly along at least one defined scan path using at least one of said carriage and said robotic arm;
    return the removed NDI probe assembly to said storage device upon completion of the NDI of the structural features of the component associated with the removed NDI assembly; and
    said system further programmed to repeat the operation, placement, execution, movement and returning for each of said NDI probe assemblies within said storage device needed to complete a specific set of NDI tests for a plurality of structural features associated with the component.

9. The NDI system of claim 8 wherein each said NDI probe assembly comprises:
    a first probe assembly half;
    a second probe assembly half; and
    at least one guide bar utilized to mechanically connect said probe assembly halves, said second probe assembly half being movable with respect to said first probe assembly half, each said probe assembly half comprising at least one magnet disposed therein, said magnets operable to move said second probe assembly half such that said NDI probe assembly properly engages the portion of the component that is to undergo NDI.

10. The NDI system of claim 8 further comprising a water tank proximate said linear track, said linear track positioned proximate said water tank such that said robotic arm is capable of traveling the length of said water tank along said linear track.

11. The NDI system of claim 8 wherein said electronic assemblies are communicatively coupled to the corresponding said transducers both when said NDI probe assemblies are deployed on said robotic arm and when disposed within said storage device.

12. The NDI system of claim 8 wherein said NDI probe assemblies comprise:
    an upper radius and cap probe assembly;
    a lower radius and side probe assembly; and
    an inner radius probe assembly.

* * * * *